United States Patent [19]

Grinter et al.

[11] Patent Number: 6,048,995
[45] Date of Patent: Apr. 11, 2000

[54] PROCESS FOR THE PREPARATION OF DIPHOSPHONATE DERIVATIVES

[76] Inventors: Trevor John Grinter; John David Hayler; Alan Negus; Michael Anthony Harris, all of Old Powder Mills, Near Leigh, Tonbridge, Kent TN11 9AN, United Kingdom

[21] Appl. No.: 09/125,560

[22] PCT Filed: Feb. 21, 1997

[86] PCT No.: PCT/GB97/00481

§ 371 Date: Aug. 20, 1998

§ 102(e) Date: Aug. 20, 1998

[87] PCT Pub. No.: WO97/31004

PCT Pub. Date: Aug. 28, 1997

[30] Foreign Application Priority Data

Feb. 21, 1996 [GB] United Kingdom .................... 9603637

[51] Int. Cl.$^7$ ...................................................... C07F 9/40
[52] U.S. Cl. ............................................. 558/87; 558/161
[58] Field of Search ....................................... 558/87, 161

[56] References Cited

U.S. PATENT DOCUMENTS

| 5,043,330 | 8/1991 | Nguyen et al. | 514/107 |
| 5,128,331 | 7/1992 | Nguyen et al. | 514/101 |
| 5,153,183 | 10/1992 | Kawabe et al. | 514/76 |

FOREIGN PATENT DOCUMENTS

| 0 440 809 A1 | 8/1991 | European Pat. Off. . |
| WO 97/04785 | 2/1997 | WIPO . |

OTHER PUBLICATIONS

Chem. Abstracts, vol. 120 (1994), p. 1213, abstract 164485, Sugioka, T., "Preparation of diazomethylenebisphosphonic acids as agrochemicals or pharmacuticals," JP 5,247,071 (Mar. 6, 1992).

*Primary Examiner*—Michael G. Ambrose
*Attorney, Agent, or Firm*—Heslin & Rothenberg, P.C.

[57] ABSTRACT

A process for the preparation of a compound of formula I,

I

[structure of formula I: benzene ring with $R^1$, $R^2$, $R^3$ substituents and a $-CH_2-CH(P(O)(OR^4)_2)(P(O)(OR^5)_2)$ group]

wherein $R^1$ and $R^2$ are independently $C_{1-6}$ alkyl, $R^3$ is hydroxy and $R^4$ and $R^5$ are independently $C_{1-6}$ alkyl is disclosed. The process comprises reacting a compound of formula II,

II

[structure of formula II: benzene ring with $R^1$, $R^2$, $R^3$ substituents and a $-CH_2-X$ group]

wherein $R^1$, $R^2$ and $R^3$ are defined as in formula I and X is a leaving group, with a compound of formula III,

III

[structure of formula III: $CH_2(P(O)(OR^4)_2)(P(O)(OR^5)_2)$]

wherein $R^4$ and $R^5$ are independently $C_{1-6}$ alkyl, in the presence of a base.

11 Claims, No Drawings

}

PROCESS FOR THE PREPARATION OF DIPHOSPHONATE DERIVATIVES

The present invention relates to a novel process for the preparation of diphosphonate derivatives. These compounds are disclosed in U.S. Pat. No. 5,128,331 as medicaments useful for lowering plasma lipid levels or blood pressure. A preferred compound has the following formula:

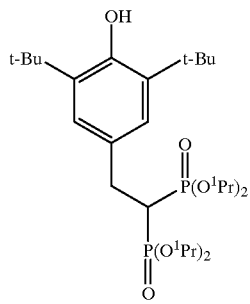

Processes for the preparation of diphosphonate compounds are also disclosed in U.S. Pat. No. 5,128,331. However, these processes suffer from a number of disadvantages, for example moderate yield, requires the use of reagents such as titanium tetrachloride which are not ideal for large scale applications, generates excess waste for disposal, etc.

Therefore there is a need for further processes for the preparation of this type of compound which are suitable for large scale use, and give the product in high yield and purity. It has now been found that diphosphonate compounds of the above structure can be prepared in a 'one-pot' procedure via reactive quinone methide intermediates which are unsubstituted at the 7-position.

In a first aspect the present invention provides a process for the preparation of a compound of formula (I):

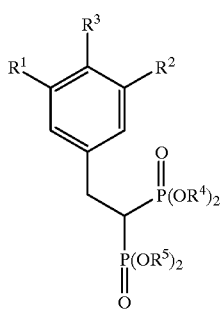

in which $R^1$ and $R^2$ are independently $C_{1-6}$ alkyl groups;

$R^3$ is hydroxy; and $R^4$ and $R^5$ are independently $C_{1-6}$ alkyl groups; which process comprises reaction of a compound of formula (II):

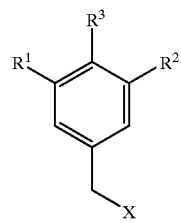

in which $R^1$, $R^2$, and $R^3$ are as defined in formula (I) and X is a leaving group, with a compound of formula (III):

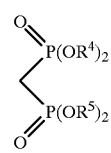

in which $R^4$ and $R^5$ are as defined in formula (I) in the presence of a base; arid optionally thereafter forming a salt.

Preferably X is a leaving group such as halo (e.g. Chloro), hydroxy, $C_{1-6}$ alkoxy, phosphate, thiol and dialkylamino groups, for example dimethylamino: or monoalkyl/monoaralkyl amino groups such as monoalkyl monobenzyl amino groups; or diaralkyl amino groups such as dibenzyl amino and substituted dibenzyl amino groups; or a quaternary ammonium group such as trimethyl ammonium, or cyclic amino such as morpholino, piperidino or anilino.

Preferably the reaction is carried out in the presence of a suitable base. Examples include metal hydrides such as sodium and lithium hydride and metal hydroxides, particularly alkali metal hydroxides such as sodium hydroxide and metal alkoxides such as sodium t-butoxide. Other suitable bases are organometallic bases, for example grignard reagents such as methylmagnesium halides and organolithium bases such as alkyl and aryl lithium compounds, e.g. methyhlithium, buyllithium and phenyllithium.

Preferably the reaction is carried out in a suitable organic solvent. The organic solvent is generally a non-protic solvent, which may be polar or non polar. Examples of suitable solvents includes alkanes such as hexane or heptane, cyclic and acylic mono- and di-ethers such as dimethoxy ethane (DME) and tetrahydrofuran (THF); dimethylformamide (DMF) and aromatic hydrocarbons such as toluene and xylene. The reaction can be carried out at reduced, ambient or elevated temperature.

The solvent is preferably substantially free from water.

Optimum reaction conditions are dependent on the nature of the leaving group X, the reaction temperature and the solvent. When X is halo or a quaternary ammonium group, preferred solvents include n-hexane. Preferably the coupling reaction is carried out at reduced or ambient temperature, for example, from about −40° C. to about 25° C.

When X is hydroxy or dialkylamino preferred solvents include 1,2-dimethoxyethane and heptane. Preferably the coupling reaction is carried out at elevated temperature, most preferably at the reflux temperature of the mixture.

Most preferably X is dialkylamino, in particular dimethylamino and the reaction is carried out at a temperature of about 100° C. Most preferably the reaction is carried out in heptane under reflux in the presence of sodium t-butoxide.

In compounds of formula (I) to (II) $C_{1-6}$ alkyl groups can be straight chain or branched.

Suitably $R^1$ and $R^2$ are $C_{1-6}$ alkyl groups and can be the same or different. Preferably $R^1$ and $R^2$ are identical. Most preferably $R^1$ and $R^2$ are both t-butyl.

Suitably $R^3$ is hydroxy.

Suitably $R^4$ and $R^5$ are $C_{1-6}$ alkyl groups which can be the same or different. Preferably $R^4$ and $R^5$ are both propyl, most preferably isopropyl.

Preferred compounds of formula (I) which can be prepared using the process of the invention include tetraisopropyl 2-(3,5-di-t-butyl4-hydroxyphenyl)ethyl-1,1-diphosphonate or salts thereof.

Those skilled in the art will appreciate that compounds of formula (II) form reactive quinone methide compounds of formula (IV) in the presence of a suitable base:

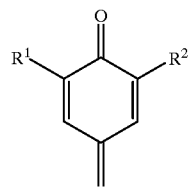

(IV)

in which $R^1$ and $R^2$ are as defined in formula (I). These compounds are highly reactive and not usually isolated. Therefore the present invention encompasses reaction of a compound of formula (IV) with a compound of formula (III) as defined above.

Compounds of formula (IV) can also be generated in situ from compounds of formula (V) and (VI):

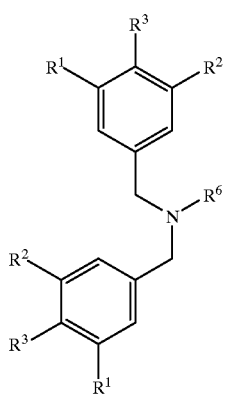

(V)

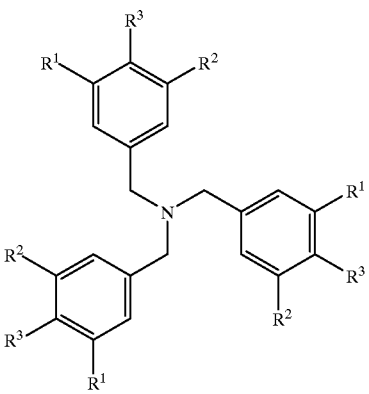

(VI)

where $R^1$, $R^2$ and $R^3$ are as defined in formula (I) and $R^6$ is hydrogen or $C_{1-6}$ alkyl. Compounds of formulae (V) and (VI) are reacted with 2 or 3 equivalents respectively of compounds of formula (III) and base.

Compounds of formulae (II) and (III) are commercially available or can be prepared using standard procedures.

Preferred salts of compounds of formula (I) are pharmaceutically acceptable salts which can be prepared using standard procedures.

The following examples illustrate the invention. The best mode of carrying out the invention currently known to the inventors is set forth in Example 3.

EXAMPLE 1

Tetraisopropyl 2-(3,5-di-t-butyl-4-hydroxyphenyl)ethyl-1,1-diphosphonate

Tetraisopropyl methylenediphosphonate (3.44 g, 0.01 mole) was added over 5 minutes to a suspension of sodium hydride (0.42 g, 0.01 mole of a 60% w/w dispersion in oil) in 1,2-dimethoxyethane (20 mL) at 20° C. 2,6-Di-t-butyl-4-hydroxymethylphenol (1.18 g, 0.005 mole) was added and the mixture stirred under nitrogen at ambient temperature for 21 hours during which time no reaction occurred. After 45 minutes at reflux HPLC analysis indicated complete consumption of the starting materials. The cooled mixture was poured into 2M aqueous hydrochloric acid (20 mL) and extracted with n-hexane (2×20 mL). The combined extracts were washed with water, dried over magnesium sulphate and evaporated to give 2.52 g, 90% yield, of the title compound.

$^1$H NMR consistent with reference spectrum.

EXAMPLE 2

Tetraisopropyl 2-(3,5-di-t-butyl-4-hydroxyphenyl)ethyl-1,1-diphosphonate

Tetraisopropyl methylenediphosphonate (19.9 g, 0.055 mole) in n-heptane (100 mL) was added over 5 minutes to a suspension of sodium hydride (2.3 g of 60% dispersion in oil 0.0575 mole) in n-heptane (100 ml). After stirring for 5 minutes a solution of 2,6-di-t-butyl-α-(dimethylamino)-4-cresol (13.15 g, 0.05 mole) in n-heptane (150 mL) was added and the resulting mixture stirred under reflux for 22 hours. After cooling to 50° C., dilute hydrochloric acid (100 mL) was added and the mixture separated. The organic phase was washed with warm water (2×100 mL) and concentrated to half volume at atmospheric pressure and cooled. The product was filtered off, washed with cold n-heptane and dried to give 21.5 g, 76.4% yield, of the title compound.

$^1$H NMR consistent with reference spectrum.

EXAMPLE 3

Tetraisopropyl 2-(3,5-di-t-butyl-4-hydroxyphenyl)ethyl-1,1-diphosphonate

A stirred suspension of sodium t-butoxide (5.28 g, 0.055 mole) in n-heptane (100 mL) under nitrogen was treated over 5 minutes with a solution of tetraisopropyl methylenediphosphonate (21.5 g of 96% pure, 0.06 mote) in n-heptane (100 ml). On complete addition, the mixture was stirred for a further 5 minutes then treated with 2,6-di-t-butyl-α-dimethylamino-4-cresol (13.15 g, 0.05 mole). The resulting mixture was stirred and boiled under reflux, with a slow nitrogen purge passing over the reaction, for 20 hours. 1M Hydrochloric acid (100 mL) was then added to the hot reaction and the mixture extracted and separated. The organic phase was washed with hot water (2×50 mL), then dried by azeotropic distillation with a Dean and Stark head. The solution was cooled and stirred at 5° C. for 1 hour. After filtration, the residue was washed with cold n-heptane and dried in air to give 25.3 g, 90% yield, of the title compound.

$^1$H NMR consistent with reference spectrum.

EXAMPLE 4

Tetraisopropyl 2-(3,5-di-t-butyl-4-hydroxyphenyl)ethyl-1,1-diphosphonate

Tetraisopropyl methylenediphosphonate (17.4 g, 0.051 mole), was added dropwise to a stirred suspension of sodium hydride (58% in mineral oil, 2.1 g, 0.051 mol) in dry tetrahydrofuran (200 mL) at ambient temperature, under an atmosphere of dry nitrogen. The addition was maintained at such a rate so as to maintain a gentle evolution of hydrogen. On complete addition, the glassware was rinsed into the flask with tetrahydrofuran (50 mL) and the solution stirred at ambient temperature for 1 hour, then cooled to −5 to 0° C.

Triethylamine (7 mL, 0.05 mole) was added dropwise over 3 minutes to a vigorously stirred solution of 4-chloromethyl-2,6-di-t-butylphenol (12.7 g., 0.05 mole) in degassed n-hexane (200 mL) under an atmosphere of dry nitrogen, at −30 to −20° C. When the addition was complete, the addition funnel was washed through into the flask with degassed n-hexane (50 mL) and the mixture stirred for 5 minutes. The solution was diluted with degassed n-hexane (50 mL). cooled to −40° C., and filtered through an open funnel under an atmosphere of nitrogen. The filter cake was washed with degassed n-hexane (100 mL, then a further 50 mL) and the combined filtrates maintained at −40° C. The preformed tetraisopropyl methylenediphosphonate anion solution was cooled to −20° C. and added dropwise to the stirred filtrate at −30 to −20° C. over 10 minutes. On complete addition the addition funnel was rinsed into the reaction with dry tetrahydrofuran (50 mL) and the mixture stirred at −30° C. for 30 minutes. The reaction mixture was poured into 2M hydrochloric acid (1L), stirred for 10 minutes, and the phases separated. The aqueous phase was extracted with ether (3×150 mL) and the combined organic extract washed with water (3×0.5 L), dried over magnesium sulphate and evaporated under reduced pressure to give an orange/yellow solid (25.7 g). Recrystallisation from n-hexane (350 mL) afforded the title compound as a white solid 21.7 g, 77% yield.

$^1$H NMR consistent with reference spectrum.

EXAMPLE 5

Tetraisopropyl 2-(3,5-di-t-butyl-4-hyydroxyphenyl)ethyl-1,1-diphosphonate

A solution of sodium t-butoxide (8.1 g, 84 mmole) in 1,2-dimethoxyethane (85 mL) was added dropwise, over 16 minutes, to a stirred, cooled, mixture of 4-chloromethyl-2,6-di-t-butylphenol (10.7 g, 42 mmole) and tetraisopropyl merhylenediphosphonate (14.5 g, 42 mmole in n-hexane (254 mL), under an atmosphere of dry nitrogen. (The temperature being maintained at −25° C. throughout the addition). When the addition was complete, the mixture was stirred for 30 minutes, poured into 2M hydrochloric acid (85 mL) and the mixture stirred. The phases were separated and the aqueous phase extracted with ethyl acetate (66 mL). The combined organic phases were washed with water (3×11 mL) filtered, and evaporated under reduced pressure to remove 170 mL of distillate. n-Hexane (85 mL) was added and the mixture distilled at ambient pressure until 90 mL of distillate had been collected. Additional n-hexane (85 mL) was added and a further 75 mL collected by distillation. The resulting solution was allowed to cool to ambient temperature, with stirring, and the precipated solid collected by filtration, washed with cold n-hexane (3×10 mL), and air dried to give a white solid, 12.8 g. The filtrate was concentrated to 75 mL by distillation at ambient pressure and the resulting solution cooled and stirred at room temperature for 1 hour. The solid obtained was filtered, washed with cold n-hexane (2×10 mL) and air dried to give a second crop of white solid, 1.97 g. The combined yield of product was 14.77 g 62.5% yield.

$^1$H NMR consistent with reference spectrum.

EXAMPLE 6

Tetraisopropyl 2-(3,5-di-t-butyl-4-hydroxyphenyl)ethyl-1,1-diphosphonate

Iodomethane (1.2 mL, 19 mmole) was added dropwise to a solution of 2,6-di-t-butyl-α-dimethylamino-4-cresol (5 g, 19 mmole) in tetrahydrofuran (100 mL) at ambient temperature, under an atmosphere of dry nitrogen, and the mixture stirred at ambient temperature for 40 minutes. The suspension was diluted with tetrahydrofuran (60 mL) and added dropwise over 40 minutes to a stirred mixture of tetraisopropyl methylenediphosphonate 17.23 g, 21 mmole) and sodium hydride (57% suspension in mineral oil, 1.6 g, 38 mmole) in dry tetrahydrofuran (50 mL). (The anion was preformed by addition of the tetraisopropyl methylenediphosphonate to the sodium hydride in THF under nitrogen and the resulting mixture stirred for 1 hour). When the addition of the salt was complete, the funnel was rinsed through into the reaction with tetrahydrofuran (20 mL) and the resultant mixture stirred at ambient temperature for 90 minutes. The reaction mixture was added dropwise over 20 minutes, to stirred, cooled. 2M hydrochloric acid (500 mL) and the glassware rinsed in with tetrahydrofuran (50 mL). When the addition was complete, the mixture was stirred for 10 minutes and then extracted with ether (4×25 mL). The combined organic extracts were washed with water (4×250 mL), saturated brine (2×250 mL), dried over magnesium sulphate and evaporated under reduced pressure to a brown syrup. 10.6 g. The syrup was dissolved in boiling n-hexane (50 mL) and allowed to cool to ambient temperature with stirring, and maintained at 0–5° C. overnight. The precipitated solid was collected by filtration, washed with ice-cold pentane and air-dried to give the title compound as an off-white solid 7.6 g, 71% yield.

$^1$H NMR consistent with reference spectrum.

EXAMPLE 7

Tetraisopropyl 2-(3,5-di-t-butyl-4-hydroxyphenyl)ethyl-1,1-diphosphonate

A solution of tetraisopropyl methylenediphosphonate (1.9 g, 5.5 mmole) in n-heptane (5 mL) was added dropwise, over 10 minutes, to a stirred suspension of sodium hydride (60% in mineral oil, 0.4 g, 0.01 mol) in n-heptane (10 mL) at ambient temperature. When the addition was complete, the glassware was rinsed into the reaction with n-heptane (5 mL), and the mixture stirred for 5 minutes at ambient temperature and then heated to reflux (98° C.) when a solution of 4-chloromethyl-2,6-di-t-butylphenol (1.27 g, 0.005 mole) in n-heptane (5 mL) was added dropwise, over 35 minutes. (The addition was at such a rate so as to maintain a gentle gas evolution). When the addition was complete, the addition funnel was rinsed into the reaction with n-heptane (5 mL) and the mixture stirred at reflux for 15 minutes, and then cooled to ambient temperature over 1 hour. The cooled mixture was poured into 2M hydrochloric acid (50 mL), with cooling, and stirred for 10 minutes. The mixture was diluted with ethyl acetate (50 mL) and the phases separated. The aqueous phase was extracted with n-heptane (50 mL, then a further 25 mL) and the combined organic extracts washed with water (3×50 mL), dried over magnesium sulphate and evaporated under reduced pressure to a yellow solid, 2.73 g. Recrystallisation from n-hexane (25 mL) afforded the title compound as a white solid 2.1 g, 74.6% yield.

Preparation of N,N-di-[3,5-di-t-butyl-4-hydroxybenzyl]methylamine

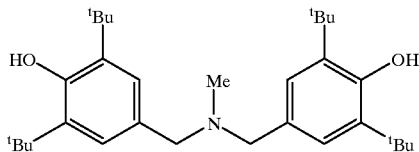

2,6-di-t-butylphenol (10.3 g, 0.05 moles) was dissolved in ethanol (75 mL) and treated with a solution of methylamine in industrial methylated spirit (7.8 mL@33% w/w methylamine, 0.065 moles). Aqueous formaldehyde solution (5.3 ml@37% w/v formaldehyde, 0.065 moles) was added and the mixture heated under reflux for 4 hours, by which time a white solid had separated. After cooling the solid was isolated by filtration, washed with acetone and dried to yield 4.5 g, 38% yield.

EXAMPLE 8

Tetraisopropyl 2-(3,5-di-t-butyl-4-hydroxyphenyl)ethyl-1,1-diphosphonate

Sodium t-butoxide (1.05 g, 0.011 mole) was suspended in n-heptane (25 mL) and treated with a solution of tetraisopropyl methylenediphosphonate (4.35 g, 0.012 moles) in n-heptane (25 mL) over 5 minutes. The mixture was stirred for a further 10 minutes, N,N-di-(3,5-di-t-butyl-4-hydroxybenzyl)methylamine (2.33 g, 0.005 moles) added and the resultant mixture stirred under reflux for 3 hours. The reaction mixture was cooled, washed with 1M hydrochloric acid solution (20 mL), water (2×10 ml) and dried over anhydrous magnesium sulphate. Filtration and evaporation gave a solid which was recrystallised from n-heptane (30 ml). Filtration and drying gave 3.95 g, 70% yield, of the title compound.

Preparation of tri-(3,5-di-t-butyl-4-hydroxybenzyl)amine

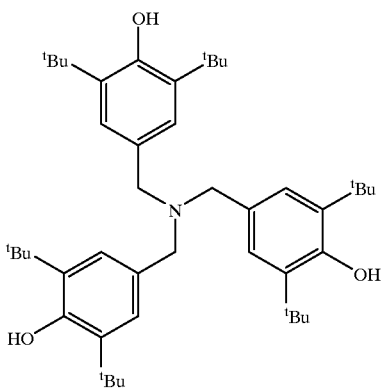

A solution of 3,5-di-t-butyl-4-hydroxybenzyl chloride (6.7 g, 0.026 moles) in dichloromethane (50 mL) was added slowly to a solution of ammonia gas in dichloromethane (200 mL) at −15 to −20° C. The mixture was allowed to warm to ambient temperature and left to stand overnight. The reaction mixture was filtered, the filtrate washed with water 3×100 mL) and dried over anhydrous magnesium sulphate. Filtration and evaporation gave a yellow solid which was recrystallised from n-heptane to yield 4.2 g, 37% yield of the title compound.

EXAMPLE 9

Tetraisopropyl 2-(3,5-di-t-butyl-4-hydroxyphenyl)ethyl-1,1-diphosphonate Sodium t-butoxide (1.05 g, 0.011 moles) was suspended in n-heptane (25 mL) and treated with a solution of tetraisopropyl methylenediphosphonate (4.35 g, 0.012 moles) in n-heptane (25 mL) over 5 minutes. The mixture was stirred for a further 10 minutes and tri-(3,5-di-t-butyl-4-hydroxybenzyl)amine (2.33 g, 0.033 moles) added with a further portion of n-heptane (25 mL). The mixture was heated under reflux for 4.5 hours, cooled, washed with 1M hydrochloric acid solution (20 mL), and water (2×10 mL). After azeotropic distillation to dry the solution the volume of the solution was reduced to approximately 50 mL. On cooling the product crystallised and after filtration and drying 3.93 g, 70% yield, of the title compound was isolated.

$^1$H NMR consistent with reference spectrum.

Preparation of 4-methoxymethyl-2,6-di-t-butylphenol

A solution of 4-hydroxymethyl-2,6-di-t-butylphenol (0.5 g) in methanol (10 mL) containing 1 drop of concentrated hydrochloric acid was stirred at ambient temperature for 1 hour. Evaporation of the solvent gave the title compound, 0.5 g, 94% yield as a white crystalline solid.

$^1$H NMR consistent with the desired material.

EXAMPLE 10

Tetraisopropyl 2-(3,5-di-t-butyl-4-hydroxyphenyl)ethyl-1,1-diphosphonate

Sodium hydride (0.084 g, 0.002 mol) was added to a stirred solution of 4-methoxymethyl-2,6-di-t-butylphenol (0.25 g, 0.001mol) and tetraisopropyl methylenediphosphonate (0.43 g, 0.00125 mol) in 1,2-dimethoxyethane (5 ml). The resulting solution was heated at 45° C. for 80 minutes and 55° C. for 160 minutes. On cooling to 20° C. the mixture was added to 2M hydrochloric acid (10 ml) and extracted with ethyl acetate/hexane. The organic extract was washed with water and evaporated to give 0.45 g (80%) of the title compound.

$^1$H NMR consistent with the desired material.

Preparation of 4-acetoxymethyl-2,6-di-t-butylphenol

A mixture of 4-chloromethyl-2,6-di-t-butylphenol (2.55 g) and potassium acetate (0.98 g) in acetone (30 mL) was stirred at 20° C. for 24 hours. After evaporation of the solvent the residue was partioned between water and n-hexane. The hexane extract was concentrated and the residue slurried in n-hexane (6 mL) at about 0° C. The crystals were collected via filtration and dried to give 1.54 g, 45% yield, of the title compound.

$^1$H NMR consistent with the desired material.

EXAMPLE 11

Tetraisopropyl 2-(3,5-di-t-butyl-4-hydroxyphenyl)ethyl-1,1-diphosphonate

Tetraisopropyl methylenediphosphonate (0.25 g, 0.00072 mole) was added to a stirred suspension of sodium hydride (0.029 g, 0.00072 mole) in 1,2-dimethoxyethane (3 mL) and the mixture heated to 50° C. 4-Acetoxymethyl-2,6-di-t-butylphenol (0.2 g) was added and the resulting mixture heated under reflux for 30 minutes. When cool n-hexane (5 mL) and 2M hydrochloric acid (1 mL) were added and the phases separated. The organic extract was washed with water (3×1 mL), dried over magnesium sulphate and evaporated to give 0.26 g, 64% yield of the title compound.

$^1$H NMR consistent with reference spectrum.

It is claimed:

1. A process for the preparation of a compound of formula (I):

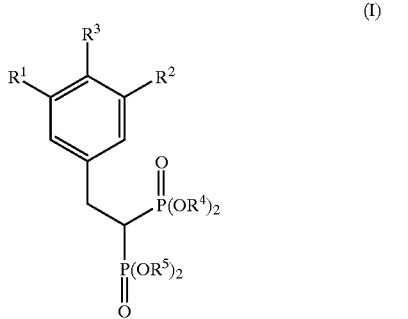

in which

R$^1$ and R$^2$ are independently C$_{1-6}$ alkyl groups;

R$^3$ is hydroxy; and

R$^4$ and R$^5$ are independently C$_{1-6}$ alkyl groups; which process comprises the reaction of a compound of formula (II):

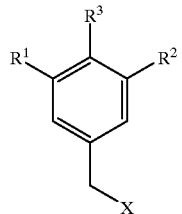

in which R$^1$, R$^2$ and R$^3$ are as defined in formula (I) and X is a leaving group selected from hydroxy and dialkylamino, with a compound of formula (III):

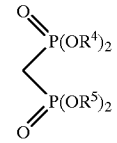

in which R$^4$ and R$^5$ are as defined in formula (I) in the presence of a base.

2. A process according to claim 1 in which the base is a metal hydride, a metal hydroxide or a metal alkoxide.

3. A process according to claim 2 in which the base is selected from sodium hydride, lithium hydride and alkali metal hydroxides.

4. A process according to claim 1 wherein the reaction is carried out in an organic solvent.

5. A process according to claim 4 wherein the solvent is selected from alkanes, aromatic hydrocarbons, cyclic or acyclic mono- or di-ethers, and dimethylformamide.

6. A process according to claim 5 in which the solvent is selected from hexane, heptane, dimethoxyethane (DME), dimethylformamide (DMF), tetrahydrofuran (THF) and toluene.

7. A process according to claim 1 in which R$^4$ and R$^5$ are both isopropyl.

8. A process according to claim 1 in which the compound prepared is tetraisopropyl 2-(3,5-di-t-butyl-4-hydroxyphenyl)ethyl-1,1-diphosphonate or a salt thereof.

9. A process according to claim 1 for preparing tetraisopropyl 2-(3,5-di-t-butyl-4-hydroxyphenyl)ethyl-1,1-diphosphonate which comprises reacting tetraisopropyl methylene-diphosphonate in an alkane with 2,6-di-t-butyl-α-dimethylamino-4-cresol in the presence of a base.

10. A process according to claim 9 wherein the alkane is n-heptane.

11. A process according to claim 9 wherein the base is sodium t-butoxide.

* * * * *